United States Patent [19]

Stetter et al.

[11] Patent Number: 4,659,366
[45] Date of Patent: Apr. 21, 1987

[54] 2-(ALKOXIMINOALKOXYCARBONYL)-PHENYLSULPHONYLUREA HERBICIDES AND FUNGICIDES

[75] Inventors: Jörg Stetter, Wuppertal; Robert R. Schmidt, Bergisch-Gladbach; Hans-Joachim Santel, Cologne; Gerd Hänssler; Ludwig Eue, both of Leverkusen, all of Fed. Rep. of Germany

[73] Assignee: Bayer Aktiengesellschaft, Leverkusen, Fed. Rep. of Germany

[21] Appl. No.: 716,869

[22] Filed: Mar. 27, 1985

[30] Foreign Application Priority Data

Apr. 10, 1984 [DE] Fed. Rep. of Germany ....... 3413490

[51] Int. Cl.$^4$ ................... A01N 43/54; A61K 31/505; C07D 239/48
[52] U.S. Cl. .......................... 71/92; 71/88; 71/93; 514/245; 514/275; 514/283; 514/284; 544/211; 544/321; 544/332; 548/263; 548/264; 548/265; 548/268; 558/3; 558/7; 558/301; 560/12; 560/13
[58] Field of Search ........................ 544/211, 321, 332; 514/245, 275, 382, 384; 71/92, 93, 88; 548/264, 265, 268, 263; 558/3, 7, 301; 560/12, 13

[56] References Cited

U.S. PATENT DOCUMENTS

| 4,370,480 | 1/1983 | Levitt et al. | 544/320 |
| 4,372,778 | 2/1983 | Levitt | 71/94 |
| 4,394,506 | 7/1983 | Levitt | 544/321 |

FOREIGN PATENT DOCUMENTS

| 0030433 | 6/1981 | European Pat. Off. |
| 0034431 | 8/1981 | European Pat. Off. |

Primary Examiner—Glennon H. Hollrah
Assistant Examiner—James H. Turnipseed
Attorney, Agent, or Firm—Sprung Horn Kramer & Woods

[57] ABSTRACT

Herbicidally and fungicidally active novel 2-(alkoximinoalkoxycarbonyl)-phenylsulphonylureas of the formula

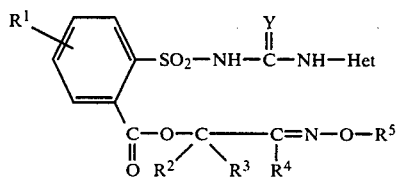

in which
$R^1$ represents hydrogen, halogen, alkyl, halogenoalkyl, alkoxy or nitro,
$R^2$ represents hydrogen, alkyl or optionally substituted aryl,
$R^3$ represents hydrogen or alkyl,
$R^4$ represents hydrogen, alkyl, alkoxy, alkylthio, alkoxyalkyl, alkylthioalkyl, cyano, alkoxycarbonyl or optionally substituted aryl,
$R^5$ represents hydrogen, alkyl, alkenyl, alkinyl, halogenoalkyl, halogenoalkenyl, alkoxyalkyl, alkylthioalkyl or optionally substituted aralkyl,
Y represents oxygen or sulphur and
Het represents a heterocyclic radical of the formula

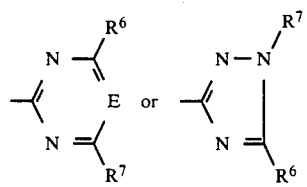

wherein
E represents nitrogen or the CH group and
$R^6$ and $R^7$ independently of one another each represent alkyl, alkoxy or alkoxyalkyl.

10 Claims, No Drawings

2-(ALKOXIMINOALKOXYCARBONYL)-PHENYL-SULPHONYLUREA HERBICIDES AND FUNGICIDES

The invention relates to new 2-(alkoximinoalkoxycarbonyl)-phenylsulphonylureas, several processes for their preparation and their use as herbicides and fungicides.

It is already known that certain 2-(oxycarbonyl)-phenylsulphonylureas, such as, for example, N-[2-(methoxycarbonyl)-phenylsulphonyl]-N'-(4,6-dimethyl-pyrimidin-2-yl)urea, have herbicidal properties (compare U.S. Pat. No. 4,394,506 or EP-OS (European Published Specification) 34,431).

However, the herbicidal action of these compounds towards important harmful plants and also their tolerance towards important crop plants is not always completely satisfactory in all fields of use.

Nothing is yet known of a fungicidal action of the 2-(oxycarbonyl)-phenylsulphonylureas which are already known.

New 2-(alkoximinoalkoxycarbonyl)-phenylsulphonylureas of the general formula (I)

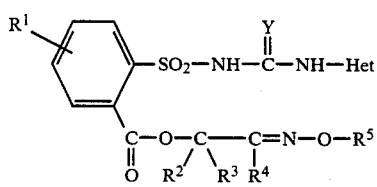

in which
R$^1$ represents hydrogen, halogen, alkyl, halogenoalkyl, alkoxy or nitro,
R$^2$ represents hydrogen, alkyl or optionally substituted aryl,
R$^3$ represents hydrogen or alkyl,
R$^4$ represents hydrogen, alkyl, alkoxy, alkylthio, alkoxyalkyl, alkylthioalkyl, cyano, alkoxycarbonyl or optionally substituted aryl,
R$^5$ represents hydrogen, alkyl, alkenyl, alkinyl, halogenoalkyl, halogenoalkenyl, alkoxyalkyl, alkylthioalkyl or optionally substituted aralkyl,
Y represents oxygen or sulphur and
Het represents a heterocyclic radical of the formula

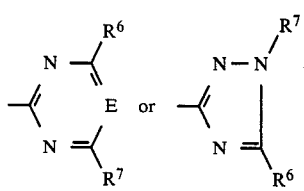

wherein
E represents nitrogen or the CH group and
R$^6$ and R$^7$ independently of one another each represent alkyl, alkoxy or alkoxyalkyl, have been found.

It has furthermore been found that the new 2-(alkoximinoalkoxycarbonyl)-phenylsulphonylureas of the general formula (I)

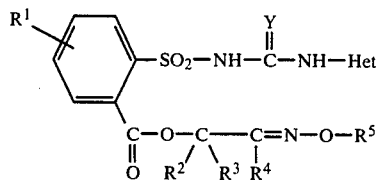

in which
R$^1$ represents hydrogen, halogen, alkyl, halogenoalkyl, alkoxy or nitro,
R$^2$ represents hydrogen, alkyl or optionally substituted aryl,
R$^3$ represents hydrogen or alkyl,
R$^4$ represents hydrogen, alkyl, alkoxy, alkylthio, alkoxyalkyl, alkylthioalkyl, cyano, alkoxycarbonyl or optionally substituted aryl,
R$^5$ represents hydrogen, alkyl, alkenyl, alkinyl, halogenoalkyl, halogenoalkenyl, alkoxyalkyl, alkylthioalkyl or optionally substituted aralkyl,
Y represents oxygen or sulphur and
Het represents a heterocyclic radical of the formula

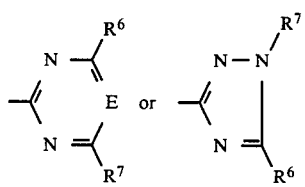

wherein
E represents nitrogen or the CH group and
R$^6$ and R$^7$ independently of one another each represent alkyl, alkoxy or alkoxyalkyl, are obtained by a process in which
(a) heterocyclic amino compounds of the formula (II)

 Het—NH$_2$  (II)

in which
Het has the abovementioned meaning, are reacted with 2-(alkoximinoalkoxycarbonyl)-phenylsulphonyl iso(thio)cyanates of the formula (III)

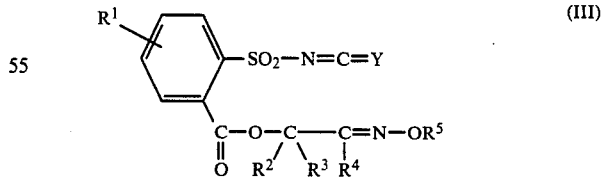

in which
R$^1$, R$^2$, R$^3$, R$^4$, R$^5$ and Y have the abovementioned meaning,
if appropriate in the presence of a diluent and if appropriate in the presence of a basic catalyst, or in which
(b) 2-(alkoximinoalkoxycarbonyl)-phenylsulphonamides of the formula (IV)

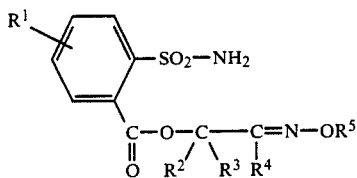

(IV)

in which
R¹, R², R³, R⁴ and R⁵ have the abovementioned meaning, are reacted with (thio)carbamates of the formula (V)

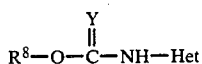

(V)

in which
Y and Het have the abovementioned meaning and
R⁸ represents alkyl or aryl, in each case if appropriate in the presence of a diluent and in each case if appropriate in the presence of a base.

Finally, it has been found that the new 2-(alkoximinoalkoxycarbonyl)-phenylsulphonylureas of the formula (I) have herbicidal properties, in particular selective herbicidal properties, and fungicidal properties.

Surprisingly, the new 2-(alkoximinoalkoxycarbonyl)-phenylsulphonylureas of the formula (I) have a considerably better tolerance towards important crop plants, coupled with an equally good herbicidal action against important harmful plants, than the 2-(oxycarbonyl)-phenylsulphonylureas known from the prior art, such as, for example, N-[2-(methoxycarbonyl)-phenylsulphonyl]-N'-(4,6-dimethylpyrimidin-2-yl)-urea, which is a closely related compound chemically and from the point of view of its action.

Moreover, the new 2-(alkoximinoalkoxycarbonyl)-phenylsulphonylureas of the formula (I) completely surprisingly also have an outstanding fungicidal action.

Formula (I) provides a general definition of the new 2-(alkoximinoalkoxycarbonyl)-phenylsulphonylureas. Preferred compounds of the formula (I) are those in which R¹ represents hydrogen, fluorine, chlorine, bromine, iodine, trifluoromethyl, nitro or in each case straight-chain or branched alkyl or alkoxy with in each case up to 4 carbon atoms, R² represents hydrogen, or represents straight-chain or branched alkyl with up to 8 carbon atoms, or represents aryl which has 6 to 10 carbon atoms and is optionally substituted by identical or different substituents, possible substituents on the aryl being: halogen, cyano, nitro and in each case straight-chain or branched alkyl, alkoxy or halogenoalkyl with in each case up to 4 carbon atoms and, where appropriate, up to 9 identical or different halogen atoms, R³ represents hydrogen, or represents straight-chain or branched alkyl with up to 4 carbon atoms, R⁴ represents hydrogen or cyano, or represents in each case straight-chain or branched alkyl, alkoxy, alkylthio, alkoxyalkyl, alkylthioalkyl or alkoxycarbonyl with in each case up to 6 carbon atoms in the individual alkyl parts, or represents aryl which has 6 to 10 carbon atoms and is optionally monosubstituted or polysubstituted by identical or different substituents, possible substituents on the aryl being those mentioned in the case of R², R⁵ represents hydrogen, or represents in each case straight-chain or branched alkyl, alkenyl, alkinyl, alkoxyalkyl, alkylthioalkyl, halogenoalkyl or halogenoalkenyl with in each case up to 6 carbon atoms in the individual alkyl, alkenyl or alkinyl parts and, where appropriate, up to 9 identical or different halogen atoms, or represents straight-chain or branched aralkyl which has up to 4 carbon atoms in the alkyl part and 6 to 10 carbon atoms in the aryl part and is optionally monosubstituted or polysubstituted by identical or different substituents in the aryl part, possible substituents on the aryl being those mentioned in the case of R², Y represents oxygen or sulphur, Het represents a heterocyclic radical of the formula

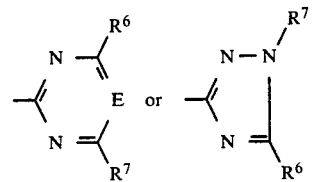

wherein
E represents nitrogen or the CH group and
R⁶ and R⁷ independently of one another represent in each case straight-chain or branched alkyl, alkoxy or alkoxyalkyl with in each case up to 6 carbon atoms in the individual alkyl parts.

Particularly preferred compounds of the formula (I) are those
in which

R¹ represents hydrogen, fluorine, chlorine, bromine, nitro, methyl, ethyl, n- or i-propyl, trifluoromethyl, methoxy or ethoxy, R² represents hydrogen, methyl, ethyl, n- or i-propyl or n-, i-, s- or t-butyl, or represents phenyl which is optionally mono-, di- or tri-substituted by identical or different substituents from the group comprising fluorine, chlorine, bromine, cyano, methyl, ethyl, methoxy, ethoxy and trifluoromethyl, R³ represents hydrogen, methyl, ethyl, n- or i-propyl, or n-, i-, s- or t-butyl, R⁴ represents hydrogen, cyano, methyl, ethyl, n- or i-propyl, n-, i-, s- or t-butyl, methoxy, ethoxy, n- or i-propoxy, methylthio, ethylthio, n- or i-propylthio, methoxymethyl, methoxyethyl, ethoxyethyl, methylthiomethyl, methylthioethyl, ethylthioethyl, methoxycarbonyl or ethoxycarbonyl, or represents phenyl which is optionally mono-, di- or tri-substituted by identical or different substituents from the group comprising fluorine, chlorine, bromine, cyano, nitro, methyl, ethyl, methoxy, ethoxy and trifluoromethyl, R⁵ represents hydrogen, methyl, ethyl, n- or i-propyl, n-, i-, s- or t-butyl, allyl, butenyl, propargyl, methoxymethyl, methoxyethyl, ethoxyethyl, methylthiomethyl, methylthioethyl, ethylthioethyl, chloroallyl or dichloroallyl, or represents benzyl or phenethyl, in each case optionally mono-, di- or tri-substituted in the phenyl part by identical or different substituents from the group comprising fluorine, chlorine, bromine, cyano, nitro, methyl, ethyl, methoxy, ethoxy and trifluoromethyl, Y represents oxygen or sulphur and Het represents a heterocyclic radical of the formula

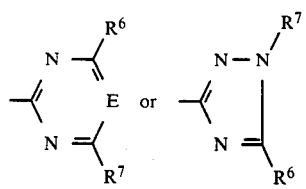

wherein
  E represents nitrogen or the CH group and
  R⁶ and R⁷ independently of one another each represent methyl, ethyl, methoxy, ethoxy, methoxymethyl, ethoxymethyl, methoxyethyl or ethoxyethyl.

The following sulphonylureas of the general formula (I) may be mentioned specifically, in addition to the compounds mentioned in the preparation examples:

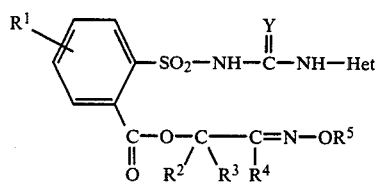

(I)

TABLE 1

| $R^1$ | $R^2$ | $R^3$ | $R^4$ | $R^5$ | Y | Het |
|---|---|---|---|---|---|---|
| H | CH₃ | H | H | CH₃ | S | pyrimidine-4,6-diCH₃ |
| H | CH₃ | H | H | H | S | pyrimidine-4-OCH₃, 6-CH₃ |
| H | CH₃ | H | H | CH₃ | O | pyrimidine-4,6-diOCH₃ |
| H | CH₃ | H | H | CH₃ | O | triazine-4,6-diCH₃ |
| H | CH₃ | H | H | CH₃ | S | triazine-4,6-diOCH₃ |

TABLE 1-continued

| $R^1$ | $R^2$ | $R^3$ | $R^4$ | $R^5$ | Y | Het |
|---|---|---|---|---|---|---|
| H | CH₃ | H | H | CH₃ | O | triazine-4-OCH₃, 6-CH₃ |
| H | CH₃ | H | H | CH₃ | S | N-methyl-triazole-OCH₃, CH₃ |
| H | CH₃ | CH₃ | H | CH₃ | O | pyrimidine-4,6-diOCH₃ |
| H | CH₃ | CH₃ | H | CH₃ | O | pyrimidine-4,6-diCH₃ |
| H | CH₃ | CH₃ | H | CH₃ | O | triazine-4-OCH₃, 6-CH₃ |
| H | CH₃ | CH₃ | H | CH₃ | O | pyrimidine-4,6-diCH₃-triazine |
| H | CH₃ | CH₃ | H | CH₃ | O | pyrimidine-4-CH₃, 6-OCH₃ |
| H | CH₃ | CH₃ | H | CH₃ | O | pyrimidine-4-OCH₃, 6-CH₃ |
| H | CH₃ | CH₃ | H | CH₃ | S | pyrimidine-4,6-diOCH₃ |
| H | CH₃ | CH₃ | H | CH₃ | O | triazine-4,6-diCH₃ |

TABLE 1-continued
| R¹ | R² | R³ | R⁴ | R⁵ | Y | Het |
|---|---|---|---|---|---|---|
| H | CH₃ | CH₃ | H | CH₃ | S | 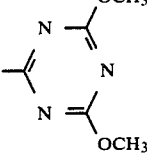 |
| H | CH₃ | CH₃ | H | CH₃ | O | 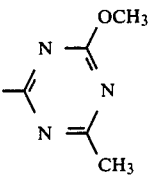 |
| H | CH₃ | CH₃ | H | CH₃ | O | 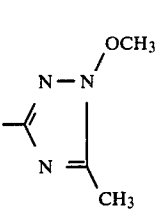 |
| H | CH₃ | H | CH₃ | CH₃ | O | 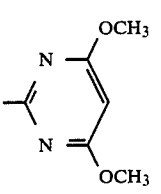 |
| H | CH₃ | H | CH₃ | CH₃ | O | 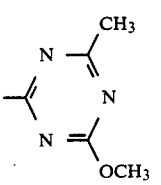 |
| H | H | H | CH₃ | CH₃ | S | 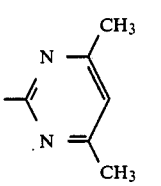 |
| H | H | H | CH₃ | CH₃ | S | 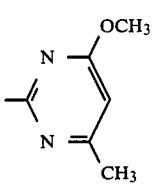 |
| H | H | H | CH₃ | CH₃ | O | 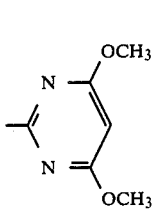 |
TABLE 1-continued
| R¹ | R² | R³ | R⁴ | R⁵ | Y | Het |
|---|---|---|---|---|---|---|
| H | H | H | CH₃ | CH₃ | O | 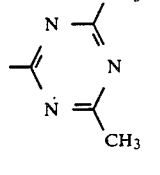 |
| H | H | H | CH₃ | CH₃ | O | 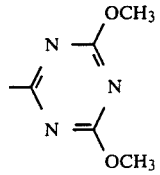 |
| H | H | H | CH₃ | CH₃ | O | 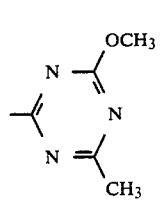 |
| H | H | H | CH₃ | CH₃ | S | 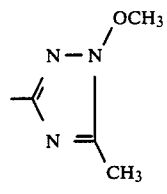 |
| H | H | H | CH₃ | CH₃ | S | 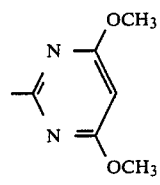 |
| H | H | H | CH₃ | CH₃ | S | 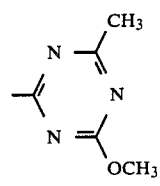 |
| H | H | H | H | CH₃ | S | 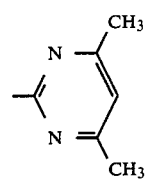 |
| H | H | H | H | CH₃ | O | 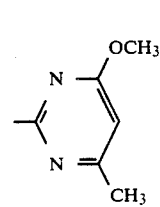 |

TABLE 1-continued
| R¹ | R² | R³ | R⁴ | R⁵ | Y | Het |
|---|---|---|---|---|---|---|
| H | H | H | H | CH₃ | O | 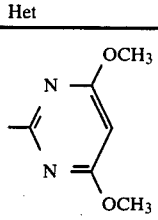 |
| H | H | H | H | CH₃ | O | 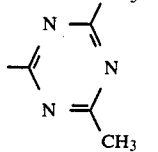 |
| H | H | H | H | CH₃ | O | 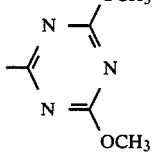 |
| H | H | H | H | CH₃ | O | 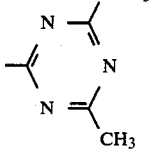 |
| H | H | H | H | CH₃ | O | 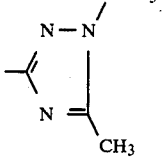 |
| H | H | H | H | CH₃ | S | 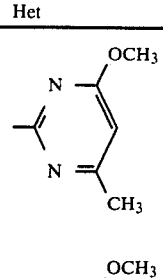 |
| H | H | H | H | CH₃ | S | 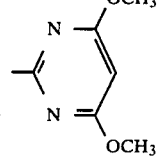 |
| H | CH₃ | CH₃ | CH₃ | CH₃ | O | 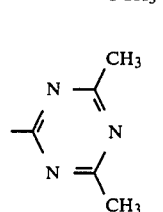 |
| H | CH₃ | CH₃ | CH₃ | CH₃ | O | 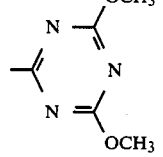 |
| H | CH₃ | CH₃ | CH₃ | CH₃ | O | 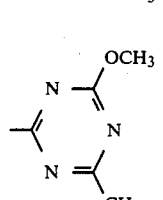 |
| H | CH₃ | CH₃ | CH₃ | CH₃ | O | 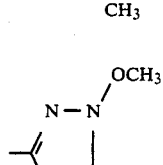 |
| H | CH₃ | CH₃ | CH₃ | CH₃ | O | 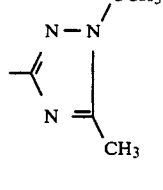 |
| H | CH₃ | CH₃ | CH₃ | CH₃ | O | 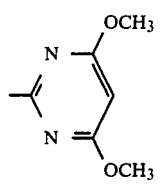 |
| H | CH₃ | CH₃ | CH₃ | CH₃ | S | 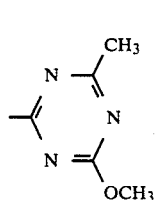 |

TABLE 1-continued
| R¹ | R² | R³ | R⁴ | R⁵ | Y | Het |
|---|---|---|---|---|---|---|
| H | H | H | H | C₂H₅ | O | 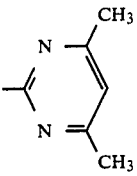 |
| H | H | H | H | C₂H₅ | O | 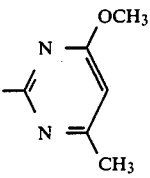 |
| H | H | H | H | C₂H₅ | O | 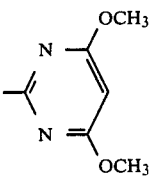 |
| H | H | H | H | C₂H₅ | O | 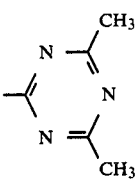 |
| H | H | H | H | C₂H₅ | O | 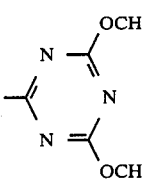 |
| H | H | H | H | C₂H₅ | O | 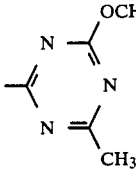 |
| H | H | H | H | C₂H₅ | O | 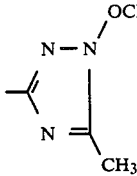 |
| H | H | H | H | C₂H₅ | S | 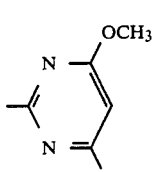 |
| H | H | H | H | C₂H₅ | S | 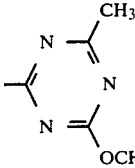 |
| H | H | H | H | —CH₂—CH=CH₂ | O | 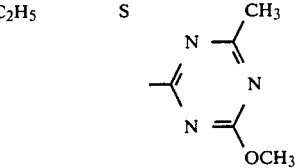 |
| H | H | H | H | —CH₂—CH=CH₂ | O | 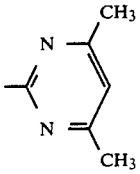 |
| H | H | H | H | —CH₂—CH=CH₂ | O | 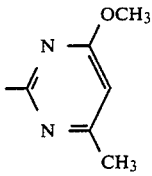 |
| H | H | H | H | —CH₂—CH=CH₂ | O | 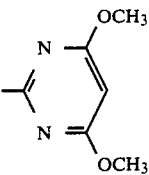 |
| H | H | H | H | —CH₂—CH=CH₂ | O | 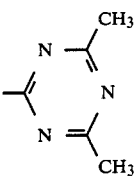 |
| H | H | H | H | —CH₂—CH=CH₂ | O | 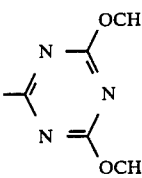 |
| H | H | H | H | —CH₂—CH=CH₂ | O | 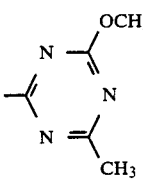 |
| H | H | H | H | —CH₂—CH=CH₂ | O | 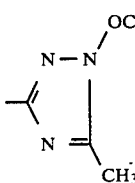 |

TABLE 1-continued

| R¹ | R² | R³ | R⁴ | R⁵ | Y | Het |
|---|---|---|---|---|---|---|
| H | H | H | H | n-C₃H₇ | O | 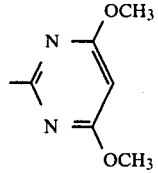 |
| H | H | H | H | n-C₃H₇ | O | 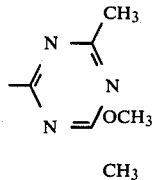 |
| H | CH₃ | H | H | —CH₂—CH=CH₂ | O | 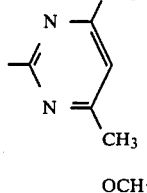 |
| H | CH₃ | H | H | —CH₂—CH=CH₂ | O | 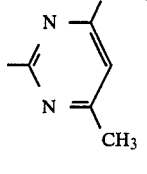 |
| H | CH₃ | H | H | —CH₂—CH=CH₂ | O | 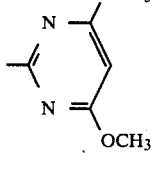 |
| H | CH₃ | H | H | —CH₂—CH=CH₂ | O | 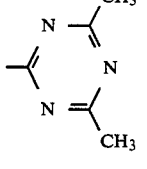 |
| H | CH₃ | H | H | —CH₂—CH=CH₂ | O | 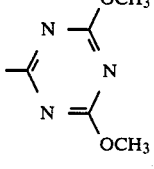 |
| H | CH₃ | H | H | —CH₂—CH=CH₂ | O | 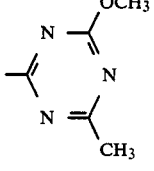 |
| H | CH₃ | H | H | —CH₂—CH=CH₂ | O | 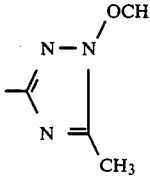 |
| H | CH₃ | H | H | —CH₂—CH=CH₂ | O | 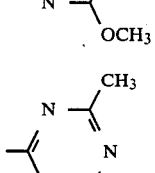 |
| H | CH₃ | H | H | n-C₃H₇ | O | 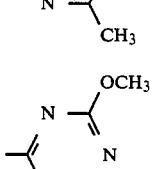 |
| H | CH₃ | H | H | n-C₃H₇ | O | 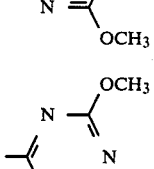 |

If, for example, 2-[(2-methoximinoethyl)-oxycarbonyl]-phenylsulphonyl isocyanate and 2-amino-4,6-dimethoxytriazine are used as starting substances, the course of the reaction in process (a) according to the invention can be represented by the following equation:

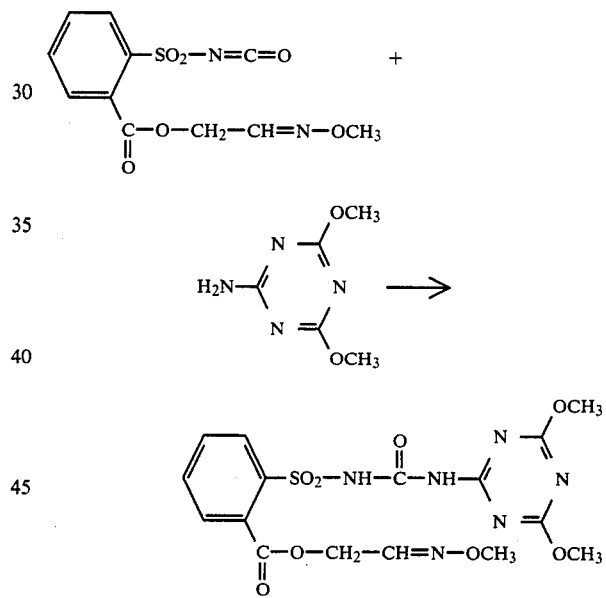

If, for example, 2-[(2-methoximinoethyl)-oxycarbonyl]-phenylsulphonic acid amide and O-phenyl N-(4-methoxy-6-methylpyrimidin-2-yl)-carbamate are used as starting substances, the course of the reaction in process (b) according to the invention can be represented by the following equation:

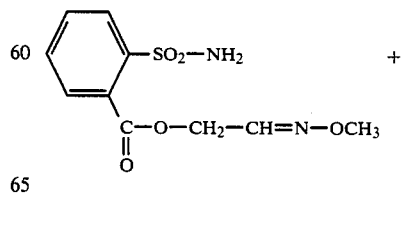

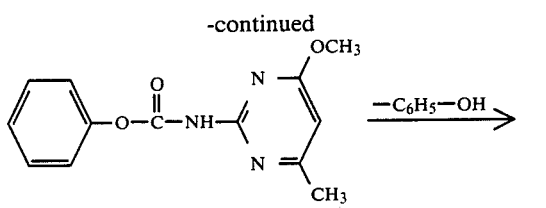

→ $-C_6H_5-OH$

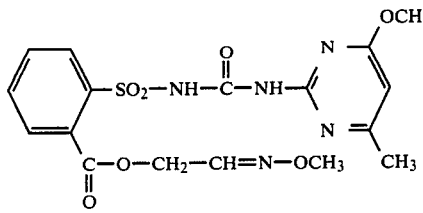

Formula (II) provides a general definition of the heterocyclic amino compounds required as starting substances for carrying out process (a) according to the invention. In this formula (II), Het preferably represents those radicals which have already been mentioned as preferred for this substituent in the description of the substances of the formula (I) according to the invention.

The heterocyclic amino compounds of the formula (II) are known. (compare, for example, European Pat. No. 73,627, European Pat. No. 73,562, European Pat. No. 85,028 and U.S. Pat. No. 4,127,405)

The novel intermediates (III) and (IV) are embraced by the formula

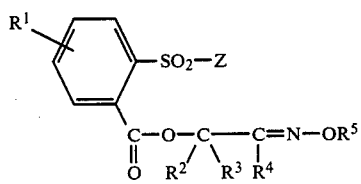

in which
R$^1$ represents hydrogen, halogen, alkyl, halo alkyl, alkoxy or nitro,
R$^2$ represents hydrogen, alkyl or optionally substituted aryl,
R$^3$ represents hydrogen or alkyl,
R$^4$ represents hydrogen, alkyl, alkoxy, alkylthio, alkoxyalkyl, alkylthioalkyl, cyano, alkoxycarbonyl or optionally substituted aryl,
R$^5$ represents hydrogen, alkyl, alkenyl, alkinyl, halogenalkyl, halogenalkenyl, alkoxyalkyl, alkylthioalkyl or optionally substituted aralkyl, and
represents —NH$_2$, —N=C= or —N=C=S.

Formula (III) provides a general definition of the 2-(alkoximinoalkoxycarbonyl)-phenylsulphonyl iso(thio)cyanates furthermore required as starting substances for carrying out process (a) according to the invention. In this formula (III), R$^1$, R$^2$, R$^3$, R$^4$, R$^5$ and Y preferably represent those radicals which have already been mentioned as preferred for these substituents in the description of the substances of the formula (I) according to the invention.

The 2-(alkoximinoalkoxycarbonyl)phenylsulphonyl iso(thio)cyanates of the formula (III) are not yet known. They are obtained by a process in which 2-(alkoximinoalkoxycarbonyl)-phenylsulphonamides of the formula (IV)

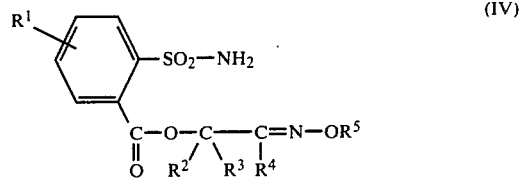

in which
R$^1$, R$^2$, R$^3$, R$^4$ and R$^5$ have the abovementioned meaning,
are reacted with phosgene or thiophosgene or with chlorosulphonyl isocyanate of the formula (VI)

$$Cl-SO_2-N=C=O \qquad (VI)$$

if appropriate in the presence of a diluent, such as, for example, chloroform or chlorobenzene, and if appropriate in the presence of an acid-binding agent, such as, for example, triethylamine, at temperatures between −30° C. and +150° C.

Formula (IV) provides a general definition of the 2-(alkoximinoalkoxycarbonyl)-phenylsulphonamides required for carrying out process (b) according to the invention and for the preparation of the starting substances of the formula (III), as intermediates. In this formula (IV), R$^1$, R$^2$, R$^3$, R$^4$ and R$^5$ preferably represent those radicals which have already been mentioned as preferred for these substituents in the description of the substances of the formula (I) according to the invention.

The 2-(alkoximinoalkoxycarbonyl)-phenylsulphonamides of the formula (IV) are also not yet known. They are obtained by a process in which 2-carboxyphenylsulphonamides of the formula (VII)

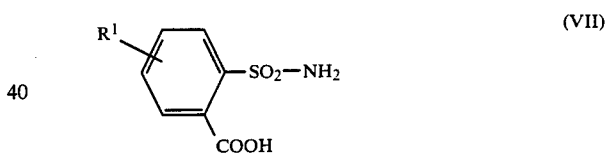

in which
R$^1$ has the abovementioned meaning, are reacted with oximinoalkyl compounds of the formula (VIII)

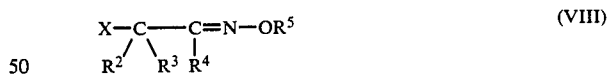

in which
R$^2$, R$^3$, R$^4$ and R$^5$ have the abovementioned meaning and
X respresents an electron-withdrawing leaving group, such as, for example, halogen, in particular chlorine or bromine, or in each case optionally substituted arylsulphonyloxy, alkylsulphonyloxy or alkoxysulphonyloxy, such as, in particular, p-toluenesulphonyloxy, methanesulphonyloxy or methoxysulphonyloxy,
if appropriate in the presence of a diluent, such as, for example, acetonitrile, and if appropriate in the presence of an acid-binding agent, such as, for example, triethylamine, at temperatures between 0° C. and +120° C.

Formula (V) provides a general definition of the (thio)carbamates furthermore required as starting substances for carrying out process (b) according to the invention. In this formula (V), Y and Het preferably represent those radicals which have already been mentioned as preferred for these substituents in the description of the substances of the formula (I) according to the invention. $R^8$ preferably represents methyl, ethyl or phenyl.

The (thio)carbamates of the formula (V) are likewise known (compare, for example, European Pat. No. 70,802, European Pat. No. 70,804, European Pat. No. 71,958, European Pat. No. 72,347 or European Pat. 79,683), or they can be prepared by known methods by simple analogous processes.

The oximinoalkyl compounds of the formula (VIII) are likewise known (compare, for example, DE-OS (German Published Specification) No. 2,922,759 or K. A. Ogloblin, V. P. Semenov, Zhurnal Organicheskoi Khimii, volume 1, No. 8 1361-1364, or K. A. Ogloblin, A. A. Potekhin, Zhurnal Obshchei Khimii, volume 34, No. 8, 2688-2693) or they are the subject of German Pat. Nos. 3,221,215, 3,220,524, 3,220,523 and 3,356,598.

They are obtained, for example, by a process in which ketones of the formula (IX)

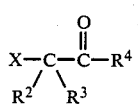

in which $R^2$, $R^3$, $R^4$ and X have the abovementioned meaning, are reacted with hydroxylamine derivatives of the formula (X)

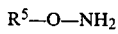

in which $R^5$ has the abovementioned meaning, or with hydro-salts thereof, if appropriate in the presence of a diluent, such as, for example, ethanol, and if appropriate in the presence of an acid-binding agent, such as, for example, potassium carbonate, at temperatures between 0° C. and +120° C.

Chlorosulphonyl isocyanate of the formula (VI), the 2-carboxyphenylsulphonic acid amides of the formula (VII), the ketones of the formula (IX) and the hydroxylamine derivatives of the formula (X) as well as their hydro-salts are generally known compounds of organic chemistry.

Preferred possible diluents for carrying out processes (a) and (b) according to the invention are inert organic solvents. These include, in particular, aliphatic or aromatic, optionally chlorinated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane or tetrahydrofuran, ketones, such as acetone or butanone, nitriles, such as acetonitrile or propionitrile, amides, such as dimethylformamide, esters, such as ethyl acetate, or sulphoxides, such as dimethylsulphoxide.

If appropriate, processes (a) and (b) according to the invention can be carried out in the presence of a base. Possible bases are all the usual inorganic or organic bases. These include, for example alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a substantial range in carrying out processes (a) and (b) according to the invention. In general, the reaction is carried out between −20° C. and +120° C., preferably between 0° C. and +50° C.

In carrying out process (a) according to the invention, in general 1.0 to 1.5 moles, preferably 1.0 to 1.2 moles, of 2-(alkoximinoalkoxycarbonyl)-phenylsulphonyl iso(thio)cyanate of the formula (III) and, if appropriate, 0.01 to 1.0 mole, preferably 0.1 to 1.0 mole, of base are employed per mole of heterocyclic compound of the formula (II).

For carrying out process (b) according to the invention, in general 1.0 to 1.5 moles, preferably 1.0 to 1.2 moles, of (thio)carbamate of the formula (V) and, if appropriate, 0.05 to 1.5 moles, preferably 0.1 to 1.0 mole, of base are employed per mole of 2-(alkoximinoalkoxycarbonyl)-phenylsulphonamide of the formula (IV).

In all the preparation processes and variants, the end products of the formula (I) are worked up and isolated in the generally customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera:
Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera:
Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera:
Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera:
Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Besides a good general herbicidal action against important harmful plants, the active compounds according to the invention also exhibit a good tolerance towards important crop plants, and can thus be used as agents for combating weeds in, for example, cotton or cereals.

In addition, when applied in appropriate amounts, the active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

the active compounds according to the invention can be used with particularly good success for combating rice diseases, such as, for example, against the rice spot disease causative organism (Pyricularia oryzae). Besides a very good protective activity, the substances according to the invention also exhibit outstanding systemic properties.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefield gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefield gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; and 4-amino-6-(1,1-dimethylethyl)-3-methylthio-1,2,4-triazin-5(4H)-one for combating weeds in soya bean. Mixtures with N,N-dimethyl-N'-(3-trifluoromethylphenyl)-urea, N,N-dimethyl-N'-(3-chloro-4-methylphenyl)-urea, N,N-dimethyl-N'-(isopropylphenyl)-urea, 4-amino-6-t-butyl-3-ethylthio-1,2,4-triazin-5(4H)-one, chloroacetic acid N-(methoxymethyl)-2,6-diethylanilide, 2-ethyl-6-methyl-N-(1-methyl-2-methoxyethyl)-chloroacetanilide, 2,6-dinitro-4-trifluoromethyl-N,N-dipropylaniline and 2-benzyloxyethyl, trimethylsilylmethyl or 2,2-diethoxyethyl 2-[4-(3,5-dichloropyrid-2-yloxy)-phenoxy]propionate are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.05 and 5 kg per ha.

When used as fungicides, the active compounds according to the invention can likewise be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The following examples serve to further illustrate the invention, without limiting it.

PREPARATION EXAMPLES

Example 1

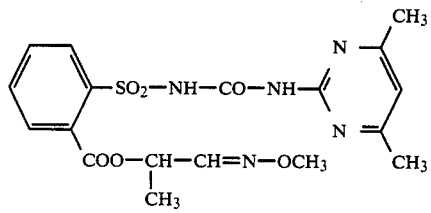

31 g (0.2 mole) of diazabicycloundecene (DBU) are added to a mixture of 58 g (0.2 mole) of 2-[1-(methoximino)prop-2-yl-oxycarbonyl]-phenylsulphonic acid amide, 50 g (0.2 mole) of O-phenyl N-(4,6-dimethylpyrimidin-2-yl)-carbamate and 300 ml of acetonitrile, with stirring, and stirring is continued for a further 20 hours at room temperature when the addition has ended. For working up, the reaction mixture is poured into 1400 ml of water, clarified with active charcoal and then acidified with 20 ml of concentrated hydrochloric acid. After 2 hours at 0° C., the precipitate is filtered off with suction and dried on clay. 54 g (62% of theory) of N-(4,6-dimethylpyrimidin-2-yl)-N'-[2-(1-methoximino-prop-2-yloxycarbonyl)-phenylsulphonyl]-urea of melting point 118° C.–127° C. are obtained.

Preparation of the starting compound

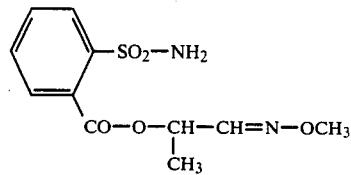

51 g (0.5 mole) of triethylamine are added dropwise to a suspension of 100 g (0.5 mole) of 2-sulphonamidobenzoic acid in 500 ml of acetonitrile, with stirring, and the mixture is then heated to 70° C. for 60 minutes and thereafter at 75° C.–80° C. for a further 15 minutes, 85 g (0.51 mole) of 2-bromo-1-methoximinopropane are then added and stirring is continued at 80° C. for a further 20 hours. For working up, the solvent is removed in vacuo, the residue is taken up in methylene chloride, the mixture is washed twice with water and dried over sodium sulphate and the solvent is removed in vacuo. 98 g (68.5% of theory) of 2-[1-(methoximino-prop-2-yl-oxycarbonyl]-phenylsulphonic acid amide of melting point 115° C.–120° C. are obtained.

Example 2

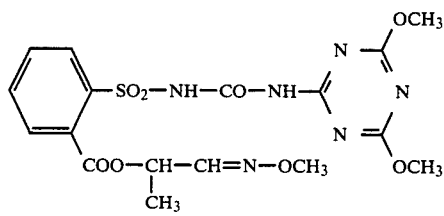

4.8 g (0.03 mole) of 2-amino-4,6-dimethoxy-1,3,5-triazine, 10 g (0.03 mole) of 2-(1-methoximinoprop-2-yloxycarbonyl)-phenylsulphonyl isocyanate and 4.5 g (0.03 mole) of diazabicycloundecene (DBU) in 100 ml of acetonitrile are stirred for 20 hours and, for working up, the mixture is poured into 500 ml of water, acidified with concentrated hydrochloric acid and extracted several times with ethyl acetate. The combined organic phases are dried over sodium sulphate and freed from the solvent in vacuo. 2.2 g (24% of theory) of N-(4,6-dimethoxy-1,3,5-triazin-2-yl)-N'-[2-(1-methoximino-prop-2-yloxycarbonyl)-phenylsulphonyl]-urea of melting point 160° C.–168° C. are obtained.

Preparation of the starting compound

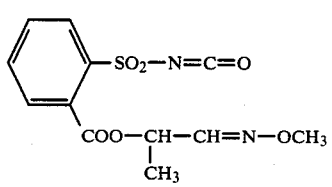

15 g (0.1 mole) of chlorosulphonyl isocyanate are added dropwise to a mixture of 29 g (0.1 mole) of 2-(1-methoximinoprop-2-yloxycarbonyl)-phenylsulphonic acid amide and 1 g (0.01 mole) of diazabicyclooctane (DABCO) in 300 ml of toluene, with stirring, and, when the addition has ended, the mixture is warmed to 90° C. to 95° C. in the course of one hour, stirred at this temperature for a further 2 hours and allowed to cool, the undissolved residue is decanted off and the mixture is concentrated in vacuo. 18 g (58 % of theory) of 2-(1-methoximinoprop-2-yloxycarbonyl)-phenylsulphonyl isocyanate are obtained as an oil.

IR: $\gamma = 2200$ cm$^{-1}$ (—N=C=O)

The following 2-(alkoximinoalkoxycarbonyl)-phenylsulphonylureas of the general formula (I) are obtained in a corresponding manner and according to the general preparation statements:

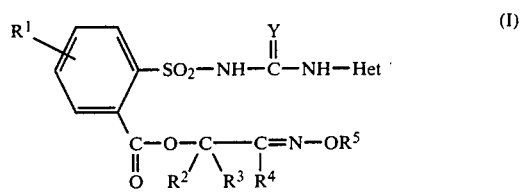

TABLE 2

| Example No. | R$^1$ | R$^2$ | R$^3$ | R$^4$ | R$^5$ | Y | Het | Physical properties |
|---|---|---|---|---|---|---|---|---|
| 3 | H | H | H | H | CH$_3$ | O | (4,6-dimethylpyrimidin-2-yl) | Melting point 120°–122° C. |
| 4 | H | H | H | CH$_3$ | CH$_3$ | O | (4-methoxy-1-methyl-pyrazol... ) | Melting point 165°–167° C. |
| 5 | H | H | H | CH$_3$ | CH$_3$ | O | (4-methoxy-6-methyl-pyrimidin-2-yl) | Melting point 135°–141° C. |
| 6 | H | H | H | CH$_3$ | CH$_3$ | O | (4,6-dimethylpyrimidin-2-yl) | Melting point 148°–150° C. |
| 7 | H | CH$_3$ | H | H | CH$_3$ | O | (4-methoxy-6-methyl-pyrimidin-2-yl) | Melting point 158°–160° C. |
| 8 | H | CH$_3$ | H | H | CH$_3$ | O | (4-methoxy-1-methyl-pyrazol...) | Melting point 183°–185° C. |

Use examples

The compounds shown below are employed as comparison substances in the use examples which follow:

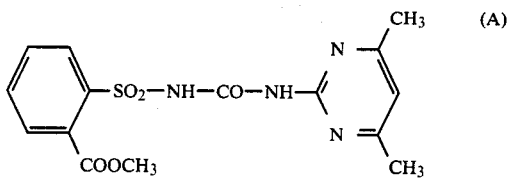

N-[2-(Methoxycarbonyl)-phenylsulphonyl]-N'-(4,6-dimethylpyrimidin-2-yl)-urea (known from EP-OS (European Published Specification) No. 34,431 or U.S. Pat. No. 4,394,506)

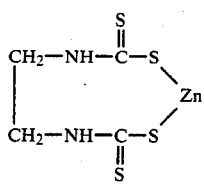

Zinc ethylene-1,2-bis(dithiocarbamate) (known from R. Wegler, 'Chemie der Pflanzenschutz- und Schädlingsbeckämpfungsmittel' ('Chemistry of the plant protection agents and agents for combating pests'), Springer Verlag Berlin, Heidelberg, New York 1970, volume 2, page 56 et seq.)

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior selectivity for crop plants, coupled with a comparable herbicidal action, is shown, for example, by the compound according to preparation Example 1.

Example B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compound according to the following preparation example: (1)

Example C

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compound according to the following preparation example: (1).

It will be understood that the specification and examples are illustrative but not limitative of the present invention and that other embodiments within the spirit and scope of the invention will suggest themselves to those skilled in the art.

We claim:

1. A 2-(alkoximinoalkoxycarbonyl)-phenylsulphonylurea of the formula

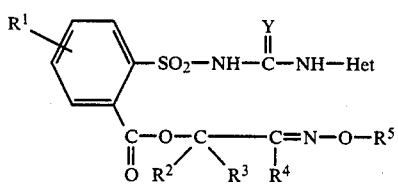

in which
$R^1$ represents hydrogen, halogen, alkyl, halogenoalkyl, alkoxy with in each case up to 4 carbon atoms or nitro,
$R^2$ represents hydrogen, alkyl with up to 8 carbon atoms or aryl which has 6 to 10 carbon atoms and is optionally substituted by halogen, cyano, nitro and/or in each case straight-chain or branched alkyl, alkoxy or halogenoalkyl with in each case up to 4 carbon atoms and, where appropriate, up to 9 identical or different halogen atoms,,
$R^3$ represents hydrogen or alkyl with up to 4 carbon atoms,
$R^4$ represents hydrogen or cyano, alkyl, alkoxy, alkylthio, alkoxyalkyl, alkylthioalkyl, alkoxycarbonyl with in each case up to 6 carbon atoms in the individual alkyl parts or aryl which has 6 to 10 carbon atoms and is optionally monosubstituted or polysubstituted by identical or different substituents, substituents on the aryl being those mentioned in the case of $R^2$ $R^5$ represents hydrogen, alkyl, alkenyl, alkinyl, halogenoalkyl, halogenoalkenyl, alkoxyalkyl, alkylthioalkyl with in each case up to 6 carbon atoms in the individual alkyl, alkenyl or alkinyl parts and, where appropriate, up to 9 identical or different halogen atoms, or aralkyl which has up to 4 carbon atoms in the alkyl part and is optionally monosubstituted or polysubstituted by identical or different substituents in the aryl part, substituents on the aryl being those mentioned in the case of $R^2$, Y represents oxygen or sulphur and Het represents a heterocyclic radical of the formula

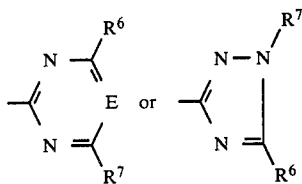

wherein

E represents nitrogen or the CH group and $R^6$ and $R^7$ independently of one another each represent alkyl, alkoxy or alkoxyalkyl with in each case up to 6 carbon atoms in the individual alkyl parts.

2. A 2-(alkoximinoalkoxycarbonyl)-phenylsulphonylurea according to claim 1, in which $R^1$ represents hydrogen, fluorine, chlorine, bromine, iodine, trifluoromethyl, nitro or in each case straight-chain or branched alkyl or alkoxy with in each case up to 4 carbon atoms, $R^2$ represents hydrogen, or represents straight-chain or branched alkyl with up to 8 carbon atoms, or represents aryl which has 6 to 10 carbon atoms and is optionally substituted by halogen, cyano, nitro and/or in each case straight-chain or branched alkyl, alkoxy or halogenoalkyl with in each case up to 4 carbon atoms and, where appropriate, up to 9 identical or different halogen atoms, $R^3$ represents hydrogen, or represent straight-chain or branched alkyl with up to 4 carbon atoms, $R^4$ represent hydrogen or cyano, or represents in each case straight-chain or branched alkyl, alkoxy, alkylthio, alkoxyalkyl, alkylthioalkyl or alkoxycarbonyl with in each case up to 6 carbon atoms in the individual alkyl parts, or represents aryl which has 6 to 10 carbon atoms and is optionally monosubstituted or polysubstituted by identical or different substituents, substituents on the aryl being those mentioned in the case of $R^2$, $R^5$ represents hydrogen, or represents in each case straight-chain or branched alkyl, alkenyl, alkinyl, alkoxyalkyl, alkylthioalkyl, halogenoalkyl or halogenoalkenyl with in each case up to 6 carbon atoms in the individual alkyl, alkenyl or alkinyl parts and, where appropriate, up to 9 identical or different halogen atoms, or represents straight-chain or branched aralkyl which has up to 4 carbon atoms in the alkyl part and 6 to 10 carbon atoms in the aryl part and is optionally monosubstituted or polysubstituted by identical or different substituents in the aryl part, substituents on the aryl being those mentioned in the case of $R^2$, and $R^6$ and $R^7$ independently of one another represent in each case straight-chain or branched alkyl, alkoxy or alkoxyalkyl with in each case up to 6 carbon atoms in the individual alkyl parts.

3. A 2-(alkoximinoalkoxycarbonyl)-phenylsulphonylurea according to claim 1, in which $R^1$ represents hydrogen, fluorine, chlorine, bromine, nitro, methyl, ethyl, n- or i-propyl, trifluoromethyl, methoxy or ethoxy, $R^2$ represents hydrogen, methyl, ethyl, n- or i-propyl, or n-, i-, s- or t-butyl, or represents phenyl which is optionally mono-, di- or tri- substituted by identical or different substituents from the group comprising fluorine, chlorine, bromine, cyano, methyl, ethyl, methoxy, ethoxy and trifluoromethyl, $R^3$ represents hydrogen, methyl, ethyl, n- or i-propyl, or n-, i-, s- or t-butyl, $R^4$ represents hydrogen, cyano, methyl, ethyl, n- or i-propyl, n-, i-, s- or t-butyl, methoxy, ethoxy, n- or i-propoxy, methylthio, ethylthio, n- or i-propylthio, methoxymethyl, methoxyethyl, ethoxyethyl, methylthiomethyl, methylthioethyl, ethylthioethyl, methoxycarbonyl or ethoxycarbonyl, or represents phenyl which is optionally mono-, di- or tri-substituted by identical or different substituents from the group comprising fluorine, chlorine, bromine, cyano, nitro, methyl, ethyl, methoxy, ethoxy and trifluoromethyl, $R^5$ represents hydrogen, methyl, ethyl, n- or i-propyl, n-, i-, s- or t-butyl, allyl, butenyl, propargyl, methoxymethyl, methoxyethyl, ethoxyethyl, methylthiomethyl, methylthioethyl, ethylthioethyl, chloroallyl or dichloroallyl, or represents benzyl or phenethyl, in each case optionally mono-, di- or tri-substituted in the phenyl part identical or different substituents from the group comprising fluorine, chlorine, bromine, cyano, nitro, methyl, ethyl, methoxy, ethoxy and trifluoromethyl, and $R^6$ and $R^7$ independently of one another each represent methyl, ethyl, methoxy, ethoxy, methoxymethyl, ethoxymethyl, methoxyethyl or ethoxyethyl.

4. A compound according to claim 1, wherein such compound is N-(4,6-dimethylpyrimidin-2-yl)-N'-[2-(1-methoximinoprop-2-yl-oxycarbonyl)-phenylsulphonyl]-urea of the formula

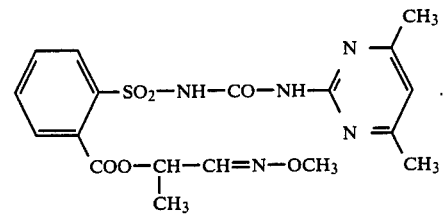

5. A herbicidal or fungicidal composition comprising a herbicidally or fungicidally effective amount of a compound according to claim 1 in admixture with a diluent.

6. A method of combating unwanted vegetation which comprises applying to such vegetation or to a locus from which it is desired to exclude such vegetation a herbicidally effective amount of a compound according to claim 1.

7. The method according to claim 6 wherein such compound is N-(4,6-dimethylpyrimidin-2-yl)-N'-[2-(1-methoximinoprop-2-yl-oxycarbonyl)-phenylsulphonyl]-urea.

8. A method of combating fungi which comprises applying to such fungi or to a fungus habitat a fungicidally effective amount of a compound according to claim 1.

9. The method according to claim 8 wherein such compound is N-(4,6-dimethylpyrimidin-2-yl)-N'-[2-(1-methoximinoprop-2-yl-oxycarbonyl)-phenylsulphonyl]-urea.

10. A compound of the formula

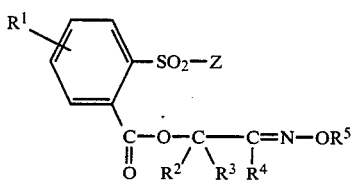

in which
$R^1$ represents hydrogen, halogen, alkyl, halogenoalkyl, alkoxy within each case up to 4 carbon atoms or nitro, $R^2$ represents hydrogen, alkyl with up to 8 carbon atoms or aryl which has 6 to 10 carbon atoms and is optionally substituted by halogen, cyano, nitro and/or in each case straight-chain or branched alkyl, alkoxy or halogenoalkyl with in each case up to 4 carbon atoms and, where appropriate, up to 9 identical or different halogen atoms, $R^3$ represents hydrogen or alkyl with up to 4 carbon atoms, $R^4$ represents hydrogen or cyano or, alkyl, alkoxy, alkylthio, alkoxyalkyl, alkylthioalkyl, alkoxycarbonyl with in each case up to 6 carbon atoms in the individual alkyl parts or aryl which has 6 to 10 carbon atoms and is optionally monosubstituted or polysubstituted by identical or different substituents, substituents on the aryl being those mentioned in the case of $R^2$, $R^5$ represent hydrogen, alkyl, alkenyl, alkinyl, halogenoalkyl, halogenoalkenyl, alkoxyalkyl, alkylthioalkyl with in each case up to 6 carbon atoms in the individual alkyl, alkenyl or alkinyl parts and, where appropriate, up to 9 identical or different halogen atoms, or aralkyl which has up to 4 carbon atoms in the alkyl part and 6 to 10 carbon atoms in the aryl part and is optionally monosubstituted or polysubstituted by identical or different substituents in the aryl part, substituents on the aryl being those mentioned in the case of $R^2$, and z represents —$NH_2$, —N=C=O or —N=C=S.

* * * * *

UNITED STATES PATENT AND TRADEMARK OFFICE
CERTIFICATE OF CORRECTION

PATENT NO. : 4,659,366

DATED : April 21, 1987

INVENTOR(S) : Jörg Stetter, et al.

It is certified that error appears in the above-identified patent and that said Letters Patent is hereby corrected as shown below:

| | |
|---|---|
| Col. 15, line 42 | Delete "halo alkyl" and substitute --halogenoalkyl-- |
| Col. 15, lines 50-51 | Correct spelling of --halogenoalkyl-- |
| Col. 15, line 51 | Correct spelling of --halogenoalkenyl-- |
| Col. 15, line 54 | Before "represents" insert --Z-- |
| Col. 15, line 54 | Delete "-N=C=" and substitute -- -N=C=O -- |
| Col. 21, line 15 | Delete "With" and substitute --with-- |
| Col. 25, lines 24-25 | Correct spelling of --Schädlingsbekämpfungsmittel-- |
| Col. 27, line 47 and Col. 30, line 16 | Delete "represent" and substitute --represents-- |
| Col. 30, line 28 | Delete "z" and substitute --Z-- |

Signed and Sealed this

Third Day of November, 1987

Attest:

Attesting Officer

DONALD J. QUIGG

Commissioner of Patents and Trademarks